(12) United States Patent
Hargrove et al.

(10) Patent No.: US 8,532,750 B2
(45) Date of Patent: Sep. 10, 2013

(54) PROCESS AND DEVICE FOR DETECTION OF PRECANCER TISSUES WITH INFRARED SPECTROSCOPY

(75) Inventors: John Taylor Hargrove, Honolulu, HI (US); Rolf Holger Wolters, Kailua, HI (US); Ulf Peter Gustafsson, Honolulu, HI (US)

(73) Assignee: STI Medical Systems, LLC, La Jolla, CA (US)

( * ) Notice: Subject to any disclaimer, the term of this patent is extended or adjusted under 35 U.S.C. 154(b) by 556 days.

(21) Appl. No.: 12/590,790

(22) Filed: Nov. 13, 2009

(65) Prior Publication Data

US 2010/0130868 A1 May 27, 2010

Related U.S. Application Data

(60) Provisional application No. 61/199,313, filed on Nov. 14, 2008.

(51) Int. Cl.
*A61B 6/00* (2006.01)

(52) U.S. Cl.
USPC .......................................................... 600/476

(58) Field of Classification Search
USPC .......................................................... 600/476
See application file for complete search history.

(56) References Cited

U.S. PATENT DOCUMENTS

| | | | |
|---|---|---|---|
| 2002/0072676 A1* | 6/2002 | Afanassieva | 600/473 |
| 2003/0078504 A1* | 4/2003 | Rowe | 600/476 |
| 2008/0221455 A1* | 9/2008 | Marshik-Geurts et al. | 600/473 |

* cited by examiner

*Primary Examiner* — Unsu Jung
*Assistant Examiner* — Saurel J Selkin
(74) *Attorney, Agent, or Firm* — Martin E. Hsia

(57) ABSTRACT

A process for determining whether tissue is precancer, in which tests discriminating between precancer and benign tissue and between precancer and normal tissue are combined, and tissue that is classified as precancer in both tests is determined to be precancer, in which neither of the tests to be combined is the most selective. Further, a process and device in which certain optimal wavelengths of glycogen, phosphate and lipid, but not protein, discriminate between normal and precancer tissues.

15 Claims, 10 Drawing Sheets

PROCESS AND DEVICE FOR DETECTION OF PRECANCER TISSUES WITH INFRARED SPECTROSCOPY

This application claims the priority of provisional patent application 61/199,313 filed Nov. 14, 2008.

TECHNICAL FIELD

This invention relates to detecting precancer tissues with infrared spectroscopy. "Precancer" includes both precancer and cancer itself "Non-precancer" includes both benign and normal tissues. This invention is applicable to all forms of cancer, but for simplicity and brevity is disclosed with respect to classifying colonic tissue among adenoma polyp (precancer tissue), hyperplastic polyp (benign tissue, from an abnormal growth), or normal mucosa (normal tissue) using absorption spectra collected with Fourier transform infrared spectroscopy ("FTIR"), or using multiple selected wavelengths of infrared light from multiple narrowband light sources (including lasers, LEDs or other devices), or tunable narrowband light sources. Thus, although disclosed with respect to classifying tissue of the colon, this invention can be used for other types of cancers to distinguish among precancer, benign and normal tissues. Further, although the invention is disclosed with respect to an endoscope, any other type of probe, including hand held probes, can be used.

Colorectal cancer is one of the major causes of morbidity and mortality in the US. About 145,000 new diagnoses and 56,000 deaths occur each year (ACS, A.C.S., Cancer Facts and Figures, 2005, *American Cancer Society*, 2005, incorporated herein by reference). If colorectal cancer can be detected at an early stage, then the 5 year survival rate is better than 90%. Unfortunately, only approximately 37% of colorectal cancers (CRC) are diagnosed in the early stages. A new technology that can detect this disease earlier, or increase the number of people screened for the disease by making the procedure safer and cheaper, could make a valuable contribution to public health.

Fourier transform infrared (FTIR) spectroscopy (described in more detail below) can be developed as a method for performing in vivo (in living tissue) histopathological (tissue changes from disease) interpretation of colonic mucosa (mucous membrane tissue) for CRC screening. The molecular information provided by FTIR spectroscopy serves as a complement to the morphological information (information relating to form and structure) provided by conventional white light colonoscopy. If precancer tissue can be detected in this molecular information before it becomes apparent in morphology, then FTIR has the potential for earlier detection than conventional colonoscopy. In that case, FTIR spectroscopy might become the primary tool for evaluation.

Instead of FTIR spectroscopy (which decomposes a continuous spectrum of infrared light into its component wavelengths), infrared light can be collected at multiple discrete wavelengths (selected for their utility in detecting precancer) from narrowband light sources (including, without limitation, lasers and infrared LEDs (light emitting diodes)). For simplicity, this will be referred to as "discrete wavelength spectroscopy."

It is anticipated that for average risk patients, visual analysis of mucosal morphology, namely the observation of polyps in the colon, will continue to serve as the first stage of screening. Polyps are growths of tissue that can be either precancer (adenoma) or benign (hyperplastic). FTIR spectroscopy (or discrete wavelength spectroscopy) has the potential to add significant value as an adjunct to colonoscopy: a second stage of screening that refines the results of visual evaluation.

The diagnostic component of colonoscopy begins with the physician's evaluation of the detailed views of most of the colonic mucosal surface provided by a white light endoscope. Biopsies and standard histopathological analysis of suspicious sites are then required in order to make clinical decisions. The fact that suspicious tissue can be excised is an advantage of colonoscopy: it is therapeutic as well as diagnostic. However, polypectomy (surgical removal of polyps) is usually performed prior to knowing the results of histopathology. The overall efficacy and efficiency of colonoscopy is diminished when the excised tissues are, in fact, normal tissues or benign tissues. Each unnecessary biopsy increases cost and risk. The cost is primarily the significant expense of histopathological evaluation, while the risks are post-polypectomy bleeding and respiratory depression from prolonged conscious sedation. If an instrument with sufficient sensitivity and specificity for precancer and cancer can be developed, biopsies can be replaced with colonic site evaluations using FTIR spectroscopy and/or discrete wavelength spectroscopy. As a result, the probability of early detection in individual patients may be improved simply by increasing the number of colonic sites evaluated without increasing the cost and risk of the procedure from increasing the number of polyps excised. Reduced cost and risk may also mean that colonoscopy with FTIR spectroscopy (or discrete wavelength spectroscopy) can be performed on a larger number of patients than colonoscopy with conventional biopsy, thereby improving detection rates.

BACKGROUND ART

The relative positions of atomic nuclei in molecules are not fixed. A molecular vibration is a periodic distortion of a molecule from its equilibrium geometry. All the various ways the atomic nuclei in a molecule can move relative to each other can be decomposed as combinations of a few vibrational modes. These vibrational modes consist of "bends" and "stretches", both symmetric and asymmetric. As a molecule vibrates, the energy held in its chemical bonds fluctuates between discrete levels. Thus the energy required for a molecule to vibrate is quantized (comes in discrete quantities), and corresponds by Planck's Law to a specific wavelength of light that can be absorbed by the molecule. These wavelengths are generally in the infrared (IR) region of the electromagnetic spectrum.

By passing a broad-band beam of IR light through a sample of a material and recording the amount of energy absorbed at each wavelength, an absorption spectrum is obtained. The specific set of wavelengths where energy is absorbed identifies the vibrational modes and therefore the chemicals that are present in the material. FTIR spectrometers typically measure the wavelength range of 2.5 microns (micrometers, or millionths of a meter) to 25 microns. Although definitions of the subranges vary, this wavelength range generally corresponds to mid-wave to very long wave IR. When a wavelength is quoted in microns herein, that also includes approximately +/−0.1 microns.

Alternatively, a set of lasers, infrared LEDs or other narrowband light sources (or one or more tunable lasers or other tunable fixed wavelength light sources) providing light at selected specific wavelengths, can be used to obtain an absorption spectrum for only those selected specific wavelengths, to provide discrete wavelength spectroscopy. This would limit the total amount of energy used and absorbed by the material (although increasing energy at those specific wavelengths), which may be important if the material is living tissue.

IR spectra are conventionally described using wavenumber (number of waves per centimeter, the inverse of wavelength), for which the equivalent range is 400 cm$^{-1}$ to 4000 cm$^{-1}$ (400 waves per centimeter to 4000 waves per centimeter). When a wavenumber is specified herein, that also includes approximately +/− approximately 10 cm$^{-1}$. The so-called fingerprint regime is a subrange from about 900 cm$^{-1}$ to 1800 cm$^{-1}$ (approximately 5.6 microns to approximately 11.1 microns (micrometers, or millionths of a meter)) that contains the absorption bands for several important biomolecules. For a complex material such as human tissue, composed of several types of biomolecules, the absorption spectrum is like a fingerprint. The goal of this project is to use the absorption spectrum to identify the subtle tissue changes associated with transformation from normal to pre-malignant colonic mucosa.

The absorption spectrum can be measured quickly and easily with FTIR spectrometry or discrete wavelength spectrometry. Attenuated total reflectance (ATR) is a sampling technique for acquiring FTIR spectra that enables variable quantities of a material to be measured without changing the absorption, thereby permitting reproducibility. The sample is pressed into direct contact with a material such as a zinc selenide crystal in which the IR light undergoes total internal reflection. When the light reflects off the internal surface of the crystal, an evanescent wave is formed that satisfies the boundary conditions on the interface. The evanescent wave penetrates approximately 1-2 microns in human tissue. It is absorbed at wavelengths corresponding to the vibrational modes of the sample.

By replacing the ATR crystal with a fiber optic probe, FTIR spectroscopy can be utilized to analyze samples that are remote (distant) with respect to the spectrometer.

However, because the colon is long, providing sufficient IR light at the end of the probe with a broadband IR source may be difficult because of transmission loss over the length of the fiber. Accordingly, a series of lasers, LEDs or other fixed wavelength light sources (or one or more tunable lasers or other tunable fixed wavelength light sources) can be used for illumination, with wave numbers within the diagnostic subranges, or at the diagnostic wavelengths, described below. A single laser cannot be used because its wavelength (wave number) would be very narrow, so that spectra covering all the necessary wavenumbers (or wavelengths) in a subrange (see below) cannot be obtained. However, a series of lasers, infrared LEDs, or other fixed wavelength light sources (each emitting infrared light at a different diagnostic wavelength), or one or more tunable lasers (or other tunable fixed wavelength light sources), can provide the range of wavelengths (wave numbers) necessary for obtaining diagnostic spectra. Unlike conventional infrared spectroscopy, an interferometer is not used to measure the absorption signal. Fourier transformation of the raw measurement is not required with infrared spectrometry utilizing lasers, LEDs or other fixed wavelength light sources.

It is therefore an object of this invention to develop a fiber optic FTIR spectroscopy probe, or discrete wavelength probe, that can be used within the working channel of an endoscope (or other probe) to enable in vivo measurement of the absorption spectrum of colonic mucosa that, combined with spectral analysis algorithms, provides a powerful tool for detection of precancer.

DISCLOSURE OF INVENTION

This and other objects of the invention are achieved by a process for determining whether tissue is precancer, benign or normal, comprising:

obtaining a spectrum of the tissue in a first set of subranges of wave numbers, wherein said first set of subranges distinguishes between precancer tissues and benign tissues, and in a second set of subranges of wave numbers, wherein the second set of subranges distinguishes between precancer tissues and normal tissues;

first classifying the tissue as precancer tissues or benign tissues using the first set of subranges;

second classifying the tissue as precancer tissues or normal tissues using the second set of subranges; and determining that tissue is precancer tissues if the tissue is classified as precancer in both the first classifying step and the second classifying step.

It is preferred that the first subrange is not the most selective subrange for distinguishing between precancer tissues and benign tissues.

It is further preferred that the second subrange is not the most selective subrange for distinguishing between precancer tissues and normal tissues.

Preferably, both the first and second set of subranges include subranges of approximately 952-1188, 1485-1585 and 1696-1774 waves per centimeter (wavelengths of approximately 5.6 to 5.9, 6.3 to 6.7, and 8.4 to 10.5 microns).

Preferably, the first set of subranges includes a subrange of approximately 1188-1325 waves per centimeter (wavelengths of approximately 7.6 to approximately 8.4 microns).

Preferably, also, the second set of subranges includes a subrange of approximately 1325-1485 waves per centimeter (wavelengths of approximately 6.7 to approximately 7.6 microns).

It is further preferred that both of the first set of subranges and the second set of subranges are within a diagnostic region having wave numbers between 900 and 1800 waves per centimeter (or wavelengths between approximately 5.6 microns and approximately 11.1 microns).

In any of the above, it is preferred that one of the subranges is the entirety of region with wavenumbers between approximately 950 waves per centimeter and approximately 1188 waves per centimeter (wavelengths between approximately 8.4 microns and approximately 10.5 microns).

In any of the above, it is also preferred to perform preprocessing on at least one of the subranges by replacing each spectral value with its second derivative and applying a window width of approximately 27-54 waves per centimeter (wavelengths between approximately 0.3 to 0.5 microns) to at least one of the subranges.

In any of the above, it is also preferred to perform preprocessing of the first subrange by replacing each spectral value with its second derivative and applying a window width of approximately 27 waves per centimeter.

In any of the above, it is also preferred to perform preprocessing of the second subrange by replacing each spectral value with its second derivative and applying a window width of approximately 58 waves per centimeter.

Further work has disclosed an alternative, potentially better, mode of practicing this invention, using only a single test of non-precancer v. precancer (instead of benign v. precancer and normal v. precancer). FTIR spectroscopy can be used over only a single continuous subrange 1A of wave numbers, from 950 cm$^{-1}$ to 1230 cm$^{-1}$ (wavelengths from approximately 8.1 microns to approximately 10.5 microns, which is slightly broader than the original subrange 1 described above), or discrete wavelength spectroscopy can be used with between three and five wavelengths (preferably three wavelengths, then four, then five) selected from this subrange 1A and a second subrange of wavenumbers from 1690 cm$^{-1}$ to 1780 cm$^{-1}$ (wavelengths from approximately 5.6 microns to approximately 5.9 microns). In either case, detection is preferably achieved using the following set of diagnostic wave numbers, listed in order of importance, selected from subrange 1A, which correspond to vibrational modes for glycogen and the phosphate group PO$_2^-$ (which is found in RNA, DNA and phospholipids), and the second subrange, which correspond to vibrational modes for lipids:

1. 1032 waves per centimeter (wavelength approximately 9.7 microns) (a vibrational mode of glycogen)
2. 1094 waves per centimeter (wavelength approximately 9.1 microns) (a vibrational mode of phosphate group found in RNA, DNA, and phospholipids)
3. 1750 waves per centimeter (wavelength approximately 5.7 microns) (a vibrational mode of lipids)
4. 1154 waves per centimeter (wavelength approximately 8.7 microns) (a vibrational mode of glycogen)
5. 1220 waves per centimeter (wavelength approximately 8.2 microns) (a vibrational mode of phosphate group found in RNA, DNA, and phospholipids) Alternatively, the following smaller sets of wave numbers can be used for such detection:

Set of 3:
1. 1032 waves per centimeter (wavelength approximately 9.7 microns) (a vibrational mode of glycogen)
2. 1094 waves per centimeter (wavelength approximately 9.1 microns) (a vibrational mode of phosphate group found in RNA, DNA, and phospholipids)
3. 1750 waves per centimeter (wavelength approximately 5.7 microns) (a vibrational mode of lipids)

Set of 4:
1. 1032 waves per centimeter (wavelength approximately 9.7 microns) (a vibrational mode of glycogen)
2. 1094 waves per centimeter (wavelength approximately 9.1 microns) (a vibrational mode of phosphate group found in RNA, DNA, and phospholipids)
3. 1750 waves per centimeter (wavelength approximately 5.7 microns) (a vibrational mode of lipids)
4. 1154 waves per centimeter (wavelength approximately 8.7 microns) (a vibrational mode of glycogen)

Surprisingly, the most important wave numbers (or wavelengths) do not include vibrational modes for any proteins, although other important sets of wave numbers (or wavelengths) do.

FTIR spectrometry may produce better results, but lasers may provide a better signal to noise ratio at their monochromatic emitting wavelengths (which necessitates the use of discrete wavelengths) and may be more robust in a clinical setting.

BRIEF DESCRIPTION OF DRAWINGS

—FIG. 1(A) shows mean absorption spectra of colonic tissue by specimen type for a zinc selenide crystal ex vivo dataset.

BEST MODES FOR CARRYING OUT INVENTION

Example

Figures 1A, 1B:
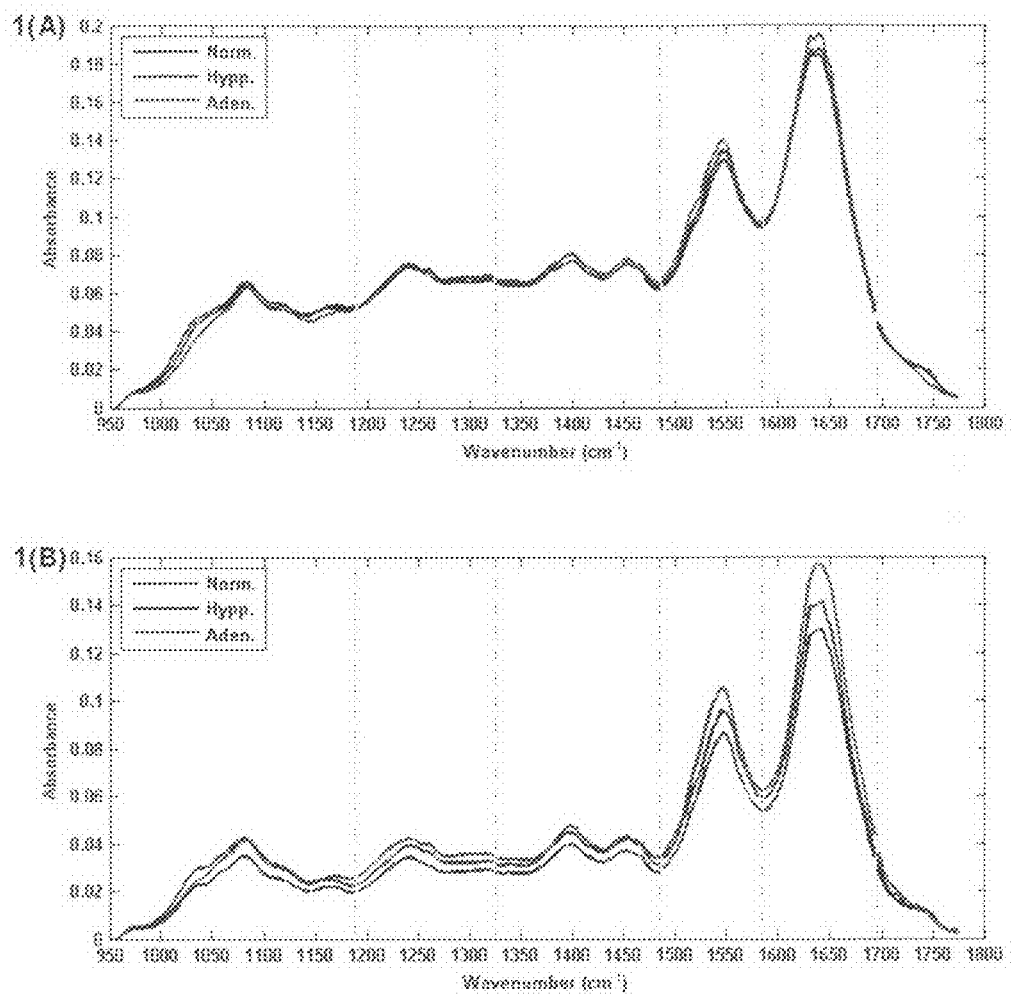
FIGS. 1(A) and (B)
FIG. 1(B) shows mean absorption spectra of colonic tissue by specimen type for a silver halide fiber optic probe in vivo dataset. Vertical dotted lines indicate division into six spectral subranges. Individual spectra were baseline-subtracted prior to averaging.

Data collection was performed at the endoscopy unit at the Stanford Medical Center and at the Veteran's Administration Palo Alto Health Care System. An endoscopy procedure was performed in the routine fashion using a standard video endoscope. When a hyperplastic or adenomatous polyp was identified on the mucosal surface by routine endoscopy, a pinch biopsy was taken of the lesion, and from an adjacent normal site. For each specimen, the gastroenterologist identified the biopsy as coming from either normal tissue or a polyp, without specifying the type of polyp. This information was recorded along with the location of each biopsy within the colon. Immediately after the endoscopic examination, the specimens were transported to the FTIR spectrometer located within the endoscopy center. Ambient water was removed from the surface of specimens by blowing cool air for approximately 10 to 20 seconds. The samples were then scanned using a Thermo Electron Nexus 470 spectrometer within a few minutes of excision to minimize degradation of the tissue.

FTIR spectra were collected using both the ATR crystal and a fiber optic probe. Both types of spectra were collected using the investigational procedure above. From September 2006 to March 2007, the FTIR spectrometer was equipped with a module utilizing a zinc selenide crystal (ZSC). Tissue specimens were placed directly upon the crystal and scanned. The spectra collected in this manner are hereafter referred to as the ZSC dataset. In June 2007, the module containing the crystal was removed from the spectrometer and replaced with a new module with connectors for a fiber optic probe. The FiberMate™, manufactured by Harrick Scientific Products, Inc., was coupled with a MultiLoop-MIR™ fiber optic probe, also manufactured by Harrick Scientific. From June to August 2007, tissue samples were scanned by holding the silver halide fiber (SHF) optic probe in contact with the specimens. The spectra collected in this manner are hereafter referred to as the SHF dataset.

Reference Diagnosis

Standard histopathology with H&E staining was performed on each biopsy specimen that was scanned. Histopathologic diagnosis was carried out by two expert pathologists, with each sample identified as hyperplastic polyp, adenoma, or normal mucosa. In order for a sample to be included in the analysis below, both pathologists had to agree on the diagnosis. Furthermore, the diagnosis of the pathologists had to be consistent with the identification of the sample as "normal" or "polyp" made by the gastroenterologist who performed the biopsy. This resulted in a total of 176 spectra from 61 patients in the ZSC dataset and 83 spectra from 33 patients in the SHF dataset. By class, in the ZSC dataset there were 85 spectra of 84 normal specimens from 48 patients, 36 spectra of 25 hyperplastic polyp specimens from 20 patients, and 55 spectra of 31 adenomatous polyp specimens from 25 patients. In the SHF dataset, there were 42 spectra of 42 normal specimens from 30 patients, 17 spectra of 16 hyperplastic polyp specimens from 13 patients, and 24 spectra of 24 adenomatous polyp specimens from 24 patients.

Spectral Range and Resolution

The FTIR spectrometer is capable of measuring spectral absorption in the wavenumber range of 400 $cm^{-1}$ to 4000 $cm^{-1}$ (2.5 to 25 microns) with a resolution of 0.965 $cm^{-1}$. For the ZSC dataset, spectra were collected at the full resolution across the entire wavenumber range. Silver halide is designed for use in the 600 $cm^{-1}$ to 2200 $cm^{-1}$ spectral range, where the absorption of this material is relatively smooth. For this reason, the SHF spectra were collected in the 600 $cm^{-1}$ to 2200 $cm^{-1}$ spectral range only. To increase signal-to-noise, SHF spectra were collected with a spectral resolution of 1.93 $cm^{-1}$. To further increase signal-to-noise and decrease computational burden, the resolution of both datasets was reduced to 3.86 $cm^{-1}$, which entailed 4× averaging of the raw ZSC spectra and 2× averaging of the SHF spectra. Finally, because an object of the present invention is to develop a fiber optic probe, the wavenumber range of ZSC data was reduced to 600 $cm^{-1}$ to 2200 $cm^{-1}$, the range of smooth absorption for a silver halide probe. With these steps, the ZSC and the SHF spectra share a common wavenumber range and resolution.

Method

Spectral Features of Colon Tissue

FIG. 1 shows the average FTIR spectra by tissue class for the ZSC and SHF datasets. Prior to averaging, each individual spectrum was adjusted by subtracting a baseline calculated as a third-order polynomial fit to the spectrum at 870 cm-1 to 970 cm-1 and 1800 cm-1 to 1940 cm-1. The absorption of the ZSC spectra is greater than for the SHF spectra due to greater absorption of the silver halide fiber. It is known that colonic FTIR spectra are pressure dependent (Rigas, B., Morgello, S., Goldman, I. S., and Wong, P. T., Human colorectal cancers display abnormal Fourier-transform infrared spectra, Proc Natl Acad Sci USA 87(20): 8140-8144, 1990, incorporated herein by reference.) The variation between datasets of the difference between tissue classes might be due to the unique way that each tissue type responds to the pressure exerted by the fiber probe. Still, the spectral peaks corresponding to specific vibrational modes are the same for both datasets.

The alteration of the biochemical composition of tissues during the onset of colonic neoplasia is a process that has been observed to produce clear FTIR spectral differences (Rigas, B., Morgello, S., Goldman, I. S., and Wong, P. T., Human colorectal cancers display abnormal Fourier-transform infrared spectra, Proc Natl Acad Sci USA 87(20): 8140-8144, 1990; Argov, S., Ramesh, J., Salman, A., Sinelnikov, I., Goldstein, J., Guterman, H., and Mordechai, S., Diagnostic potential of Fourier-transform infrared microspectroscopy and advanced computational methods in colon cancer patients, J. Biomed. Opt. 7(2): 248-254, 2002; Argov, S., Sahu, R. K., Bernshtain, E., Salman, A., Shohat, G., Zelig, U., and Mordechai, S., Inflammatory bowel diseases as an intermediate stage between normal and cancer: a FTIR-microspectroscopy approach, Biopolymers 75(5): 384-392, 2004; Bogomolny, E., Huleihel, M., Suproun, Y., Sahu, R. K., and Mordechai, S., Early spectral changes of cellular malignant transformation using Fourier transform infrared microspectroscopy, J. Biomed. Opt. 12(2): 024003, 2007, all of which are hereby incorporated herein by reference.) As cells proliferate, protein content rises relative to lipid content, glycogen and phosphate decrease, and RNA rises relative to DNA. Some of these spectral differences are apparent in FIG. 1. In these earlier studies, the spectral differences have been quantified by several simple measures. For example, the integration of absorption (area under curve) from ~950 $cm^{-1}$ to 1350 $cm^{-1}$ (wavelengths from approximately 7.4 microns to approximately 10.5 microns) has been used to demonstrate elevated phosphate content in neoplastic tissue. The phosphate peak at 1082 $cm^{-1}$ (approximately 9.1 microns) has been observed to shift to higher wavenumbers with malignant transformation. The ratio of RNA to DNA, calculated both as the absorption ratios (1121 $cm^{-1}$)/(1020 $cm^{-1}$) and (996 $cm^{-1}$)/(966 $cm^{-1}$), as well as the glycogen to protein ratio (1080 $cm^{-1}$)/(1545 $cm^{-1}$), have been shown to decrease with cell proliferation. These relatively simple spectral biomarkers have been used to differentiate adenomatous polyps, malignant cells, and normal tissue.

The Beer-Lambert Law relates the absorption of a sample to the concentration of a chemical constituent. The spectral peaks from infrared absorption of tissue can be used to calculate the concentration of biomolecular components using a calibration model. Methods for developing calibration models are within the purview of the field of chemometrics. Generally, calibration models are determined by a linear regression of the known component concentrations of a set of reference samples and the absorption spectra measured for the reference samples. Predictions using the calibration model can then be made to estimate component concentrations from unknown sample spectra. For example, Wang et al. (Wang, T. D., Triadafilopoulous, G., Crawford, J. M., Dixon, L. R., Bhandari, T., Sahbaie, P. et al., Detection of Endogenous Biomolecules in Barrett's Esophagus by Fourier Transform Infrared Spectroscopy, Proceedings of the National Academy of Sciences, 2006, incorporated herein by reference) created a set of reference standards for protein, DNA, glycogen, and glycoprotein by mixing known quantities of pure components from lyophilized powders mixed in PBS. Reference FTIR absorption spectra were collected and a calibration model estimated. These were then used to estimate the concentration of each biochemical from absorption spectra of excised esophagus, which included specimens of squamous, gastric, and Barrett's esophagus with and without dysplasia (abnormal growth). It was found that Barrett's with dysplasia had higher protein and nucleic acid concentration and lower glycogen concentration. The biomolecular concentrations were then used to classify among the three sample types, as well as to separate Barrett's with dysplasia from non-dysplasia.

Discriminant Analysis

The methods described above provide an explanation of the sources of infrared absorption in terms of physiological parameters. This is crucial for understanding the underlying processes at work. However, there are disadvantages to adopting this approach when the primary goal is simply identifying abnormal growth (dysplastic) tissue. First of all, it is not obvious if all the biochemical metrics should be used, or a subset. Nor is there generally a priori guidance for selecting a classification threshold, because the particular values of integrated absorption, ratios, or concentrations depend upon how these measures are defined, or may be expressed in arbitrary units. Classification is thus performed post hoc, once the important biochemical differences have presented themselves. Most importantly, the biochemical measures may not provide the greatest separation between tissue classes, thereby compromising performance. For these reasons, a discriminant analysis was employed to explicitly model the difference between tissue classes.

Partial Least Squares Regression

The product of discriminant analysis is a prediction of class membership instead of a measure of biochemical content. The discriminant analysis preferably used is based on partial least squares regression (Wold, S., Ruhe, A., Wold, H., and Dunn III, W. J., The collinearity problem in linear regression. The partial least squares approach to generalized inverses., SIAM J. Sci. Stat. Comput 5: 735-743, 1984; Geladi, P. and Kowalski, B. R., PLS Tutorial, Anal. Chim. Acta 185(1), 1986, incorporated herein by reference). Partial least squares (PLS, also known as projection to latent structures) is a standard tool in the field of chemometrics for processing FTIR spectra. After the spectral binning described above, there are 207 values of absorption in the fingerprint regime 950 $cm^{-1}$ to 1750 $cm^{-1}$ (approximately 5.7 microns to approximately 10.5 microns) of the FTIR spectra, a number significantly larger than the number of spectra in either dataset. Furthermore, the absorptions at various wavenumbers are highly correlated. PLS is particularly suited for problems like this, in which the system in underdetermined and the predictor variables are collinear. The underlying assumption of PLS is that the observations are generated by a process driven by a small number of latent (not directly observed) variables. In PLS the observed data are projected onto a small number of independent latent variables, addressing both the underdeterminedness and collinearity of the problem. While better-known methods based on principal components project observed data onto the most important modes of predictor variance, the latent variables of PLS are chosen to maximize the covariance of predictor variables and responses. The reduction of variance by projection of the predictor variables is therefore less likely to discard information important to the response, leading to better performance.

In partial least squares discriminant analysis (PLSDA), there is a single response variable indicating class membership. For the tissue classification with PLSDA, the latent variables presumably are the various biochemicals identified above. It is not necessary to identify them for classification with PLS. Preferably, the sequence of the methods discussed above is reversed by first developing the classification model, and then examining this model for insights to the important biochemical differences between adenomas, hyperplastic polyps, and normal mucosa.

Partial least Squares discriminant analysis (PLSDA) was implemented using the PLS_Toolbox commercial software package [Eigenvector Research, Inc.]. The PLS equations were solved using the SIMPLS algorithm (de Jong, S., SIMPLS: an alternative approach to partial least squares regression, Chemom. Intell. Lab. Syst. 18: 251-263, 1993). PLS_Toolbox is written in the MATLAB™ programming language, which allowed us to easily view, modify, and supplement the software as needed, as well as visualize the results.

Classification Algorithm Design

As noted above, it is an object of this invention to provide an endoscope-compatible instrument that can distinguish adenomas from hyperplastic polyps and normal tissue. While the more clinically relevant problem is to distinguish adenomatous from hyperplastic polyps, the possibility that normal tissue might be inadvertently sampled by the instrument cannot be ruled out. It was discovered early in the algorithm development process that the most difficult tissue types to distinguish are normal mucosa from hyperplastic polyps. Given that distinguishing these benign tissues is not clinically relevant, it was chosen not to pose the problem as one of three-class discrimination. Instead, a two-part algorithm was developed, consisting of a model to discriminate adenomas from hyperplastic polyps, and a model to distinguish adenomas from normal tissue.

Each model was developed using only the adenoma and hyperplastic polyp samples, or only the adenoma and normal samples. The two-part algorithm is simply the application of both classification models to each unknown sample. Performance of the two-part algorithm was assessed as the accuracy with which adenomas were distinguished from non-adenomas. In this way, the algorithm "wastes" none of its skill discriminating hyperplastic polyps from normal tissue. In fact, as shown below, algorithm specificity was improved when hyperplastic samples that were misidentified (as adenoma) by the hyperplastic model were rejected as adenoma by the normal model, and when normal samples that were misidentified (as adenoma) by the normal model were rejected as adenoma by the hyperplastic model.

Separate algorithms were developed for the ZSC and SHF datasets. In each dataset, there were a sufficient number of patients to permit cross-validation by leave-one-patient-out. In this method, all the samples from a single patient were set aside as the test set to assess the accuracy of the prediction model estimated from the training set consisting of the rest of the patients. This process was repeated until every patient had been tested.

To determine the final two-part algorithm, thousands of models were tested for the hyperplastic polyp vs. adenoma (HvA) component and thousands for the normal vs. adenoma (NvA) component. These candidate models were generated by varying model attributes as described below. The accuracy of each component model was assessed using cross-validation. Then the 30 most accurate HvA models and the 30 most accurate NvA models were selected. As mentioned above, for HvA models only hyperplastic polyp and adenoma samples were used, so the most accurate models were those which correctly classified the greatest number of hyperplastic polyp and adenoma samples. Similarly, for NvA models only normal and adenoma samples were used, so the most accurate models were those which correctly classified the greatest number of normal and adenoma samples. All 900 combinations of these two models were then tested as two-part algorithms on all samples, again using leave-one-patient-out cross-validation. The final algorithm described below consists of the best HvA-NvA combination in terms of sensitivity and specificity for adenoma. Surprisingly, the best HvA-NvA combination did NOT contain either the most accurate HvA model or the most accurate NvA model.

Candidate Model Exhaustive Search

As mentioned above, a large number of candidate models were evaluated for selection of the best HvA and NvA model. Unique candidate models were generated from three different sources: variation in the number of predictor variables (i.e., use of the entire spectrum or selection of a subrange), variation in preprocessing techniques, and variation in the number of latent variables included in the model. The performance of each unique combination was then assessed. The following sections describe these steps in the order in which they are applied.

Interval PLSDA

Some predictor variables may contain noise or interfering signals which may actually deteriorate the accuracy of a regression model. For example, two of the strongest absorption peaks in most tissues are C=O stretching of protein (Amide I) and O—H bending of water. These two vibrations are centered at 1650 $cm^{-1}$ and 1640 $cm^{-1}$ respectively, and overlap significantly due to their spectral width. While the protein content in a sample is an important biochemical property of the tissue, the water content is just as likely to depend on how well the specimen was dried. Therefore, the accuracy of PLSDA might be improved by discarding the spectral values around the Amide I—water peak. Because water has no other major peaks in the fingerprint regime, it can no longer act as a confounder, at the price of losing the protein information in the Amide I peak.

Interval PLSDA refers to the selection of a subset of variables that provide superior prediction compared to using all the variables in the spectrum (Wise, B. M., Gallagher, N. B., Bro, R., Shaver, J. M., Windig, W., and Koch, R. S., PLS_Toobox Version 4.0 Manual, ed. Eigenvector Research, Inc. 2006, incorporated herein by reference). Interval PLSDA is performed by conducting an exhaustive search for the best combination of variables. We performed interval PLSDA by dividing the fingerprint regime into six subranges (FIG. 1). Subrange 1 is from 950 $cm^{-1}$ to 1188 $cm^{-1}$ (wavelengths from approximately 8.4 microns to approximately 10.5 microns) and encompasses phosphate, glycogen, RNA, and DNA peaks. Phosphate peaks indicate the presence of both nucleic acids. Other peaks due to uracil and thymine indicate RNA and DNA individually. Prior studies have shown that this subrange is the most important for discriminating colon tissue (Rigas, B., Morgello, S., Goldman, I. S., and Wong, P. T., Human colorectal cancers display abnormal Fourier-transform infrared spectra, Proc Natl Acad Sci USA 87(20): 8140-8144, 1990; Argov, S., Ramesh, J., Salman, A., Sinelnikov, I., Goldstein, J., Guterman, H., and Mordechai, S., Diagnostic potential of Fourier-transform infrared microspectroscopy and advanced computational methods in colon cancer patients, J. Biomed. Opt. 7(2): 248-254, 2002; Argov, S., Sahu, R. K., Bernshtain, E., Salman, A., Shohat, G., Zelig, U., and Mordechai, S., Inflammatory bowel diseases as an intermediate stage between normal and cancer: a FTIR-microspectroscopy approach, Biopolymers 75(5): 384-392, 2004; Bogomolny, E., Huleihel, M., Suproun, Y., Sahu, R. K., and Mordechai, S., Early spectral changes of cellular malignant transformation using Fourier transform infrared microspectroscopy, J. Biomed. Opt. 12(2): 024003, 2007, all of which are hereby incorporated herein by reference). (Further interval PLSDA experiments in which Subrange 1 was further subdivided were performed, but using the entire subrange resulted in the most predictive skill). Subrange 2 is from 1188 $cm^{-1}$ to 1325 $cm^{-1}$ (wavelengths from approximately 7.6 to approximately 8.4 microns) and encompasses phosphate and Amide III protein peaks. Subrange 3 is from 1325 $cm^{-1}$ to 1485 $cm^{-1}$ (wavelengths from approximately 6.7 microns to approximately 7.6 microns) and encompasses peaks unique to the structure of specific proteins and lipids. Subrange 4 is from 1485 $cm^{-1}$ to 1585 $cm^{-1}$ (wavelengths from approximately 6.3 to approximately 6.7 microns) and contains the Amide II protein peak and another minor peak for the protein tyrosine. Subrange 5 is from 1585 $cm^{-1}$ to 1696 $cm^{-1}$ (wavelengths from approximately 5.9 to approximately 6.3 microns) and contains the Amide I protein peak and an overlapping peak for water. Subrange 6 is from 1696 $cm^{-1}$ to 1740 $cm^{-1}$ (wavelengths from approximately 5.7 to approximately 5.9 microns) and contains a lipid peak. Models were tested using all possible combinations of the 6 subranges.

Preprocessing: Second Derivative

Preprocessing is another method of removing variance from the spectral input data that is not relevant for predicting class membership. There are two basic types of preprocessing: sample-wise and variable-wise. Sample-wise methods act on each spectrum one at a time to remove unwanted variance from individual spectra. Sample-wise preprocessing methods used in this analysis include baseline subtraction, along-spectrum derivation, and normalization. Variable-wise preprocessing methods act on each spectral wavenumber independently, but require multiple samples for parameter estimation before they are implemented.

The baseline removal procedure was discussed above. This method acts as a high pass filter by removing a signal whose fundamental wavelength is the entire spectrum. An alternative to baseline removal consists of replacing each spectral value with its second derivative. This was performed by applying the Savitsky-Golay algorithm (Savitzky, A. and Golay, M. J. E., Smoothing and differentiation of data by simplified least squares procedures, Anal. Chem. 36: 1627, 1964, incorporated herein by reference) implemented in the PLS_Toolbox. A second-order polynomial was fit to a window around each value of the spectrum, and the value was then replaced with the second-order coefficient of the polynomial. Because the polynomial fit acts to smooth the data, the Savitsky-Golay algorithm is a low pass as well as a high pass filter. As is obvious in FIG. 1, the width of the spectral peaks varies greatly. For this reason experiments were conducted with window widths of 7, 11, and 15 points, or 27 $cm^{-1}$, 42 $cm^{-1}$, and 58 $cm^{-1}$ in wavenumber space. For example, better predictive skill was found by applying a 15-point second derivative to subrange 4, with the broad Amide II peak, and a 7-point second derivative to the subrange 1, with multiple narrow peaks. Other experiments with longer and shorter windows, as well as higher and lower order derivatives, found that using the above parameters resulted in the most predictive skill.

Preprocessing: Normalization

When individual samples systematically vary due to instrument effects or other observational variability, the relative values of spectral measurements often have greater predicative value than the absolute measurements. In this case, normalization is useful, and also helps all samples to have an equal impact in the model. Three different types of norm were applied in this example. Using the one-norm, each input spectral variable was divided by the sum of the absolute value of all variables to return a spectrum that sums to one. Using the two-norm, each input variable was divided by the sum of the squared variables to return a spectrum with a length of one. Using the max-norm, each input value was divided by the maximum value in the spectrum to return a spectrum whose maximum value is one.

Three different windows were used to define that input spectra for normalization. Using the complete-spectrum window, every value in a spectrum is considered as an input to the norm. Of course, due to interval PLSDA, this does not mean that the entire fingerprint regime was used, as some of the subranges may have been discarded. The point is that all spectral values are normalized together at once. Using the each-subrange window, each of the six spectral subranges was normalized independently. Finally, using the continuous-subrange window, each section of spectrum that was continuous in wavenumber was normalized independently. For example, consider the case where all spectral subranges except number 5 (Amide I) were used. Using the complete-spectrum window, all five subranges were input together for a single normalization. Using the each-subrange window, all five subranges were normalized independently. Using the continuous-subrange window, the five subranges from 950 $cm^{-1}$ to 1585 $cm^{-1}$ (wavelengths from approximately 6.3 microns to approximately 10.5 microns) were normalized together, and the lipid subrange from 1696 $cm^{-1}$ to 1740 $cm^{-1}$ (wavelengths from approximately 5.7 to 5.9 microns) was normalized by itself. Note that when in the course of interval PLSDA only a single subrange was used, all three normalization windows were equivalent.

Preprocessing: Unit-Variance Scaling

Variable-wise preprocessing methods assume that any variance in the data is valuable for prediction. Variables with low variance are weighted relative to variables with high variance so that they have equal input to the regression model. The only variable-wise preprocessing method used in this study was unit-variance scaling. In this method, each value of a spectrum (or preprocessed spectrum—unit-variance scaling always occurs as the last preprocessing step) was centered by subtracting its mean value, and then was scaled to unit variance by dividing by its standard deviation.

There are important reasons to avoid unit variance scaling if possible. Two extra components are required to apply a model developed on the calibration set to the test set. When variable-wise preprocessing is not used, a vector of regression coefficients is all that is required from the calibration model. The test spectrum, after any sample-wise preprocessing involving it alone, is simply multiplied by this vector to produce the class prediction. With unit-variance scaling, two additional vectors are required from the calibration model: the mean spectrum and the standard deviation. These are applied prior to the regression coefficient. These vectors may contain information that is unique to the calibration due to instrument or other observational effects. Thus the transfer of a calibration model from one instrument or experiment to another is inherently riskier. For these reasons, candidate models were evaluated with and without unit-variance scaling, with the idea that models without scaling would be preferred if their performance was comparable to those with scaling.

Preprocessing: Number of Candidate Models

The total number of candidate models estimated for each classification problem is the product of the interval and preprocessing combinations. For each spectral subrange of interval PLSDA, there were five options: exclude the subrange, include the subrange with baseline removal only, and include the subrange with 7, 11, or 15 point polynomial fits for second derivative. With six spectral subranges, this produced $5^6$=15,625 combinations. There were 10 normalization options derived from three types of norm, three window definitions, and a no-normalization option. Finally there were two options for unit variance scaling: use it or do not use it. The total number of preprocessing combinations was 312,500. Each combination was used for each of the four classification problems: two two-class problems (HvA and NvA) times two datasets (ZSC and SHF). Each candidate model was evaluated using leave-one-patient-out cross-validation as described above. The computations utilized a dedicated desktop personal computer for about two weeks.

Number of Latent Variables Selection

An important part of PLSDA is the selection of the number of latent variables to include in the model. It is possible to "over-fit" a PLSDA model by including too many latent variables. In this case, the model has an apparent predictive ability that is actually derived from fitting noise rather than the variability of the underlying process. The following method was used to select the number of latent variables. In general, it is best to apply parsimony and use the smallest number of latent variables as possible (Wise, B. M., Gallagher, N. B., Bro, R., Shaver, J. M., Windig, W., and Koch, R. S., PLS_Toobox Version 4.0 Manual, ed. Eigenvector Research, Inc. 2006, incorporated herein by reference). Therefore, it was assumed the number of independent biochemical processes underlying the observed spectral differences was no more than four. Each candidate model was estimated using one, two, three, and four latent variables. Each time, the mean square error of cross-validation (RMSECV) was calculated as a measure of predictive ability. RMSECV is the root mean square difference between the actual class value (arbitrarily assigned as 1 for adenoma and 2 for hyperplastic/normal) and the predicted class value for all test samples. A good rule of thumb is to exclude an additional latent variable unless it lowers the RMSECV by at least 2% (Wise, B. M., Gallagher, N. B., Bro, R., Shaver, J. M., Windig, W., and Koch, R. S., PLS_Toobox Version 4.0 Manual, ed. Eigenvector Research, Inc. 2006, incorporated herein by reference). 5% was used as the criteria. Thus for each of the 312,500 candidate models, the number of latent variables used was the highest number which reduced RMSECV of that model by 5% over the next highest, up to a maximum of four.

Two-Part Algorithm Exhaustive Search

As mentioned earlier, the candidate model exhaustive search was based on testing with either normal and adenoma samples (NvA), or hyperplastic polyp and adenoma samples (HvA). The 30 most accurate HvA models and the 30 most accurate NvA models were then selected for further testing as component of the two-part algorithm. Leave-one-patient-out cross-validation was again used, in the following way. A patient was selected as the test set. All spectra from this patient were set aside. The normal spectra and adenoma spectra from the other patients were then used as the calibration set for the NvA candidate model. Once calibrated, this model was applied to all of the test spectra, and an NvA classification value was recorded for each. Then the hyperplastic polyp and adenoma spectra from the other patients were used as the calibration set for the HvA model. Once calibrated, this model was applied to all of the test spectra, and an HvA classification value was recorded for each. All patients were rotated through as the test patient. After a complete rotation, each spectrum, regardless of its true tissue class, had two classification values: one from the HvA candidate model and one from the NvA candidate model. Classification thresholds were varied in two dimensions and the two-part algorithm was scored using histopathology as truth for adenoma and non-adenoma.

This process was repeated for all 900 combinations of NvA and HvA candidate models. The two-part algorithms presented below demonstrated the most skill in identifying adenoma samples. First the process was applied using the 30 best NvA and HvA models that did not use unit-variance scaling, for reasons described above. It was then repeated for the 30 best NvA and HvA models that did employ unit-variance scaling. The result was a final two-part algorithm that employed unit-variance scaling, and one that did not. This process was utilized for the both the ZSC and SHF datasets. Each dataset had its own unique list of the 30 best NvA and HvA candidate models.

Results

Zinc Selenide Crystal Dataset

Figure 2:
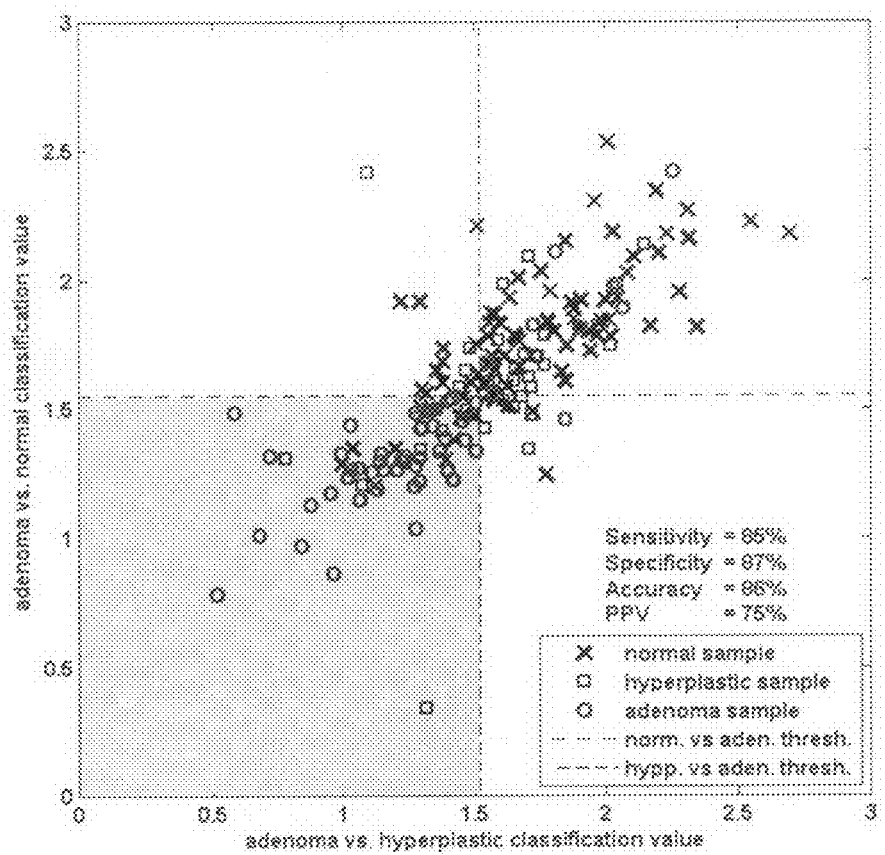
FIG. 2—Best two-part algorithm classification values for zinc selenide crystal (ZSC) dataset. The normal vs. adenoma (NvA) and hyperplastic polyp vs. adenoma (HvA) models did not employ unit-variance scaling. The optimal threshold selections for the NvA and HvA models are shown, and correspond to the dot on the ROC curve in FIG. 3. True positives for adenoma appear as circles in the shaded area. True negatives for non-adenoma appear as crosses (normal) and squares (hyperplastic) in the un-shaded area.
Figure 3:
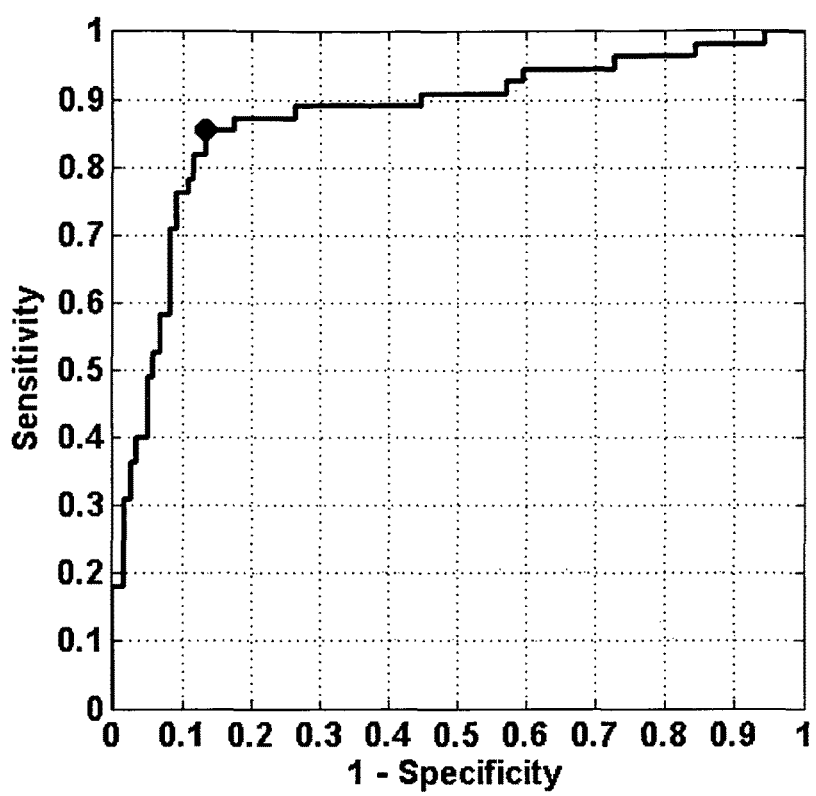
FIG. 3—Receiver operating characteristic of the best two-part algorithm without unit-variance scaling for the ZSC dataset. The dot along the curve corresponds to the threshold selections in FIG. 2.

Classification values for ZSC spectra for the best two-part algorithm that did not include unit-variance scaling are shown in FIG. 2. The optimal threshold selections for the NvA and HvA models divide the plot into four regions. True positives for adenoma appear as circles in the shaded area. True negatives for non-adenoma appear as crosses (normal) and squares (hyperplastic) in the three regions composing the un-shaded area. Adenoma was classified with a sensitivity and specificity of 85% and 87%. The accuracy was 86% and the positive predictive value (PPV) was 75%. The receiver operating characteristic (ROC) curve is shown in FIG. 3. This curve represents the optimal variation of two discrimination thresholds, and defines a path in that is not necessarily a straight line. The dot on the ROC curve in FIG. 3 represents the optimal threshold selection shown in FIG. 2.

Figures 4A, 4B, 4C:
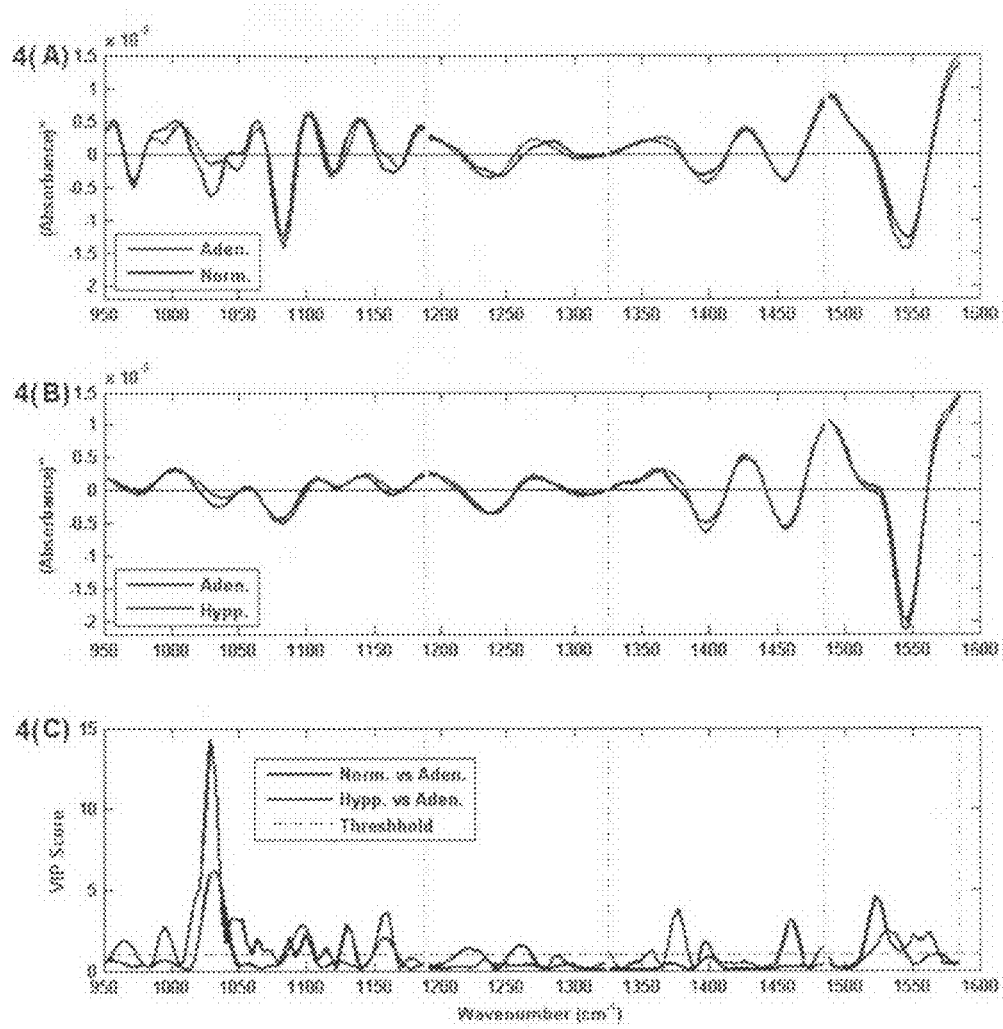
FIGS. 4(A), 4(B), and 4(C)—ZSC ex vivo dataset mean preprocessed spectra by tissue class for (A) NvA model and (B) HvA model. Spectra are divided into subranges and preprocessed without unit-variance scaling as described in text. (C) Variable importance in projection (VIP) scores for NvA and HvA models.

The spectral data for input to the PLSDA regression, the result of the exhaustive search of spectral subranges and preprocessing methods, are shown by class average in FIGS. 4(A), 4(B), and 4(C)—a for the NvA model and in FIGS. 4(A), 4(B), and 4(C)—b for the HvA model. The wavenumber axes end at 1600 cm$^{-1}$ in both of these plots because in neither case did the optimal model include the subrange 5 (Amide I—water) or subrange 6 (lipids). Both models used subranges 1-4 with Savitzky-Golay second derivatives. The length of the polynomial fit was the four subranges was 7, 15, 15, and 15 points for the NvA model, and 15, 15, 11, and 11 points for the HvA model. Neither model employed normalization. The NvA model utilized three latent variables with the HvA model utilized four.

FIGS. 4(A), 4(B), and 4(C)—c is a plot of variable importance for the projection (VIP). VIP is a summary of the importance of a variable for modeling both the variance of the predictors (the spectra) and the variance of the response (the classes) (Chong, I.-G. and Chi-Hyuck, J., Performance of some variable selection methods when multicollinearity is present, Chemom. Intell. Lab. Syst. 78: 103-112, 2005, incorporated herein by reference). By definition, the average VIP score of a PLS model is one. Variables with values much greater than one are the most important for the model, while those with values much less than one make a negligible contribution.

The maximum VIP value for both the NvA and HvA models is at the glycogen peak around 1030 cm$^{-1}$. This is expected from looking at the mean input spectra after preprocessing for each tissue class in a and b. There is a large difference between the mean preprocessed spectra of adenoma and normal (a) and hyperplastic polyp (b). Other important VIP peaks in subrange 1 are found around 1160 cm$^{-1}$ (mixed glycogen and glycoprotein peak) and 1085 cm$^{-1}$ (mixed glycogen and phosphate peak). Our results are consistent with earlier studies demonstrating that normal tissue has higher quantities of glycogen than abnormal growth (dysplastic) tissues (Rigas, B., Morgello, S., Goldman, I. S., and Wong, P. T., Human colorectal cancers display abnormal Fourier-transform infrared spectra, Proc Natl Acad Sci USA 87(20): 8140-8144, 1990; Argov, S., Ramesh, J., Salman, A., Sinelnikov, I., Goldstein, J., Guterman, H., and Mordechai, S., Diagnostic potential of Fourier-transform infrared microspectroscopy and advanced computational methods in colon cancer patients, J. Biomed. Opt. 7(2): 248-254, 2002; Argov, S., Sahu, R. K., Bernshtain, E., Salman, A., Shohat, G., Zelig, U., and Mordechai, S., Inflammatory bowel diseases as an intermediate stage between normal and cancer: a FTIR-microspectroscopy approach, Biopolymers 75(5): 384-392, 2004; Bogomolny, E., Huleihel, M., Suproun, Y., Sahu, R. K., and Mordechai, S., Early spectral changes of cellular malignant transformation using Fourier transform infrared microspectroscopy, J. Biomed. Opt. 12(2): 024003, 2007; Wang, T. D., Triadafilopoulous, G., Crawford, J. M., Dixon, L. R., Bhandari, T., Sahbaie, P. et al., Detection of Endogenous Biomolecules in Barrett's Esophagus by Fourier Transform Infrared Spectroscopy, Proceedings of the National Academy of Sciences, 2006, all of which are incorporated herein by reference). Our results demonstrate that this is true for hyperplastic polyps (neoplastic tissue) as well as normal tissue. These studies have also demonstrated that the region with wavenumbers between 900 cm$^{-1}$ and 1200 cm$^{-1}$ (wavelengths between approximately 8.3 and approximately 11.1 microns) has the greatest diagnostic value. We assessed the performance of the best two-part algorithm which utilized subrange 1 only for both the NvA and HvA components. This model discriminated adenoma and non-adenoma with an accuracy of 78%. This is only 8% less than the accuracy of the best two-part algorithm which was free to utilize the entire fingerprint regime. The ratio of RNA to DNA absorption at (996 cm$^{-1}$)/(966 cm$^{-1}$) has been demonstrated to decrease as normal colon cells become cancerous (Argov, S., Sahu, R. K., Bernshtain, E., Salman, A., Shohat, G., Zelig, U., and Mordechai, S., Inflammatory bowel diseases as an intermediate stage between normal and cancer: a FTIR-microspectroscopy approach, Biopolymers 75(5): 384-392, 2004, incorporated herein by reference). From the VIP plot of FIGS. 4(A), 4(B), and 4(C)—c, it appears that these bands have a minor role in discriminating normal tissue from adenomas. However it is worth noting that a 7-point window was used on subrange 1 for the NvA model, compared to a 15-point window for the HvA model. The shorter window retains the RNA peak at 996 cm$^{-1}$ in the data for the NvA model, resulting in some diagnostic value according to the VIP score.

In candidate model testing, the accuracy of the NvA model on normal and adenoma samples alone was 83%, and the accuracy of the HvA model on hyperplastic polyp and adenoma samples alone was 79%. Thus the accuracy of the two-part algorithm is greater than either of its components. It is in fact advantageous to define the clinically relevant problem as not just distinguishing adenomas from hyperplastic polyps, but from normal tissue as well. This was surprising as the addition of a second classifier might be expected to lower the sensitivity, as a second opportunity to produce a false negative. But in FIG. 2 there is only one adenoma sample in the upper left or lower right box: a sample that was correctly identified by one model but not by the other. All the other false negatives were missed by both models, so there was little additional cost in sensitivity in applying both. But there was a clear benefit for specificity. Crosses in the lower right box are normal samples that were misclassified by the NvA model, but were still classified as non-adenoma by the HvA model. Squares in the upper left box are hyperplastic polyp samples that were misclassified by the HvA algorithm, but were still classified as non-adenoma by the NvA model. Surprisingly also, the best combination of HvA and NvA did NOT include either the best HvA model or the best NvA model.

The overwhelming majority of non-adenomas are in the upper-right box. The absorption spectra of hyperplastic polyps and normal tissue are similar enough that algorithms optimized to detect one class also do an adequate job of detecting the other. This is because they basically utilize the same spectral features. However, the two tissue types are different enough that the algorithms assign different weights to these features. The purpose of testing all combinations of the 30 best HvA and NvA models is identify two models that are accurate within their own class, and at the same time are different enough from each other to have value for identifying the other class as non-adenoma.

Silver Halide Fiber Dataset

Figure 5:
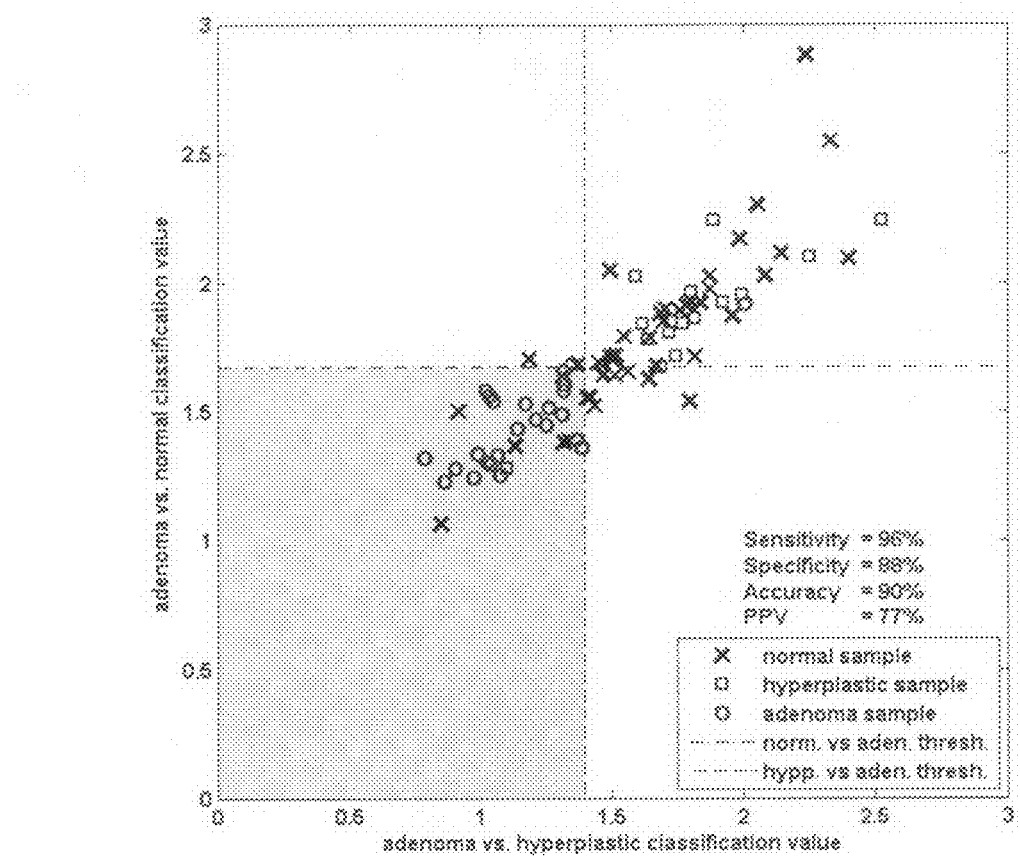
FIG. 5—Best two-part algorithm classification values for silver halide fiber (SHF) dataset. The normal vs. adenoma (NvA) and hyperplastic polyp vs. adenoma (HvA) models did not employ unit-variance scaling. The optimal threshold selections for the NvA and HvA models are shown, and correspond to the dot on the ROC curve in FIG. 6. True positives for adenoma appear as red circles in the shaded area. True negatives for non-adenoma appear as black crosses (normal) and blue squares (hyperplastic) in the un-shaded area.
Figure 6:
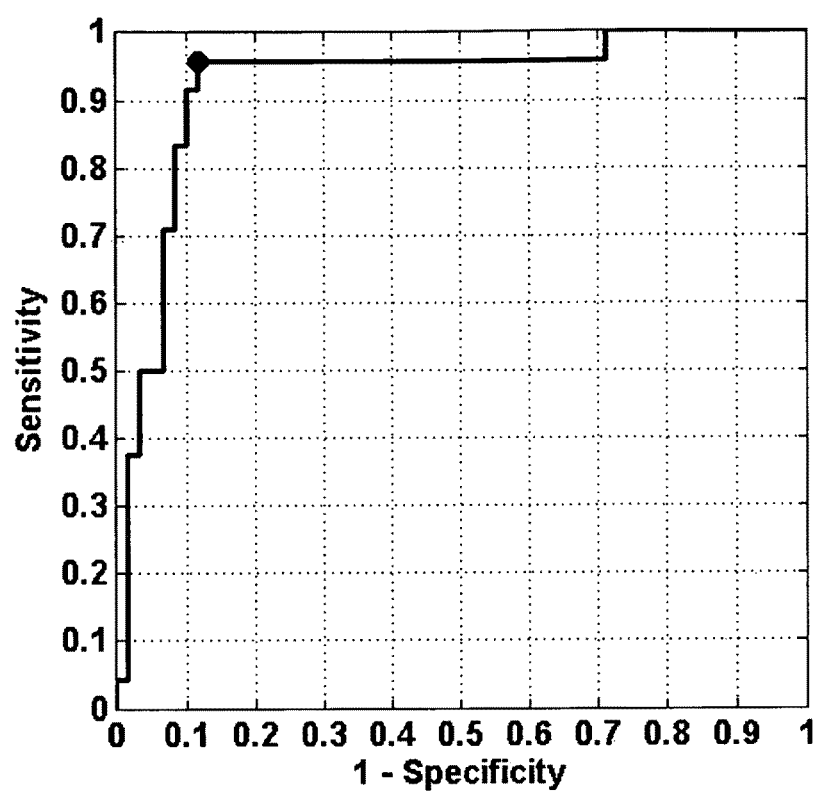
FIG. 6—Receiver operating characteristic of the best two-part algorithm without unit-variance scaling for the SHF dataset. The dot along the curve corresponds to the threshold selections in FIG. 5.

The classification values assigned to the SHF spectra for the best two-part algorithm that did not include unit-variance scaling are shown in FIG. 5. With the optimal two-dimensional threshold, adenoma was classified with a sensitivity and specificity of 96% and 88%. The accuracy was 90% and the positive predictive value (PPV) was 77%. The receiver operating characteristic (ROC) curve is shown in Please replace the fifth full paragraph on page 9 with the following:

FIG. 6. These results represent a slight improvement over the ZSC dataset.

The NvA model alone had an accuracy of 83% for normal samples. As with the ZSC dataset, a large number of normal samples misidentified by the NvA model are classified as non-adenoma by the HvA model. The HvA model alone has an accuracy of 93% for hyperplastic polyp samples. While this number is greater than the overall performance of 90% for both normal and hyperplastic polyps, close examination of FIG. 5 reveals that the two-part algorithm improved accuracy to 95% for hyperplastic polyps alone as a hyperplastic polyp sample misclassified by the HvA model was classified as non-adenoma by the NvA model.

Again, surprisingly, the best two-part algorithm did not include either the best HvA model or the best NvA model.

The improvement in classification performance for adenoma and hyperplastic polyps seen in the SHF dataset, when compared to the ZSC dataset, is also surprising and therefore shows that an endoscope compatible probe, when combined with the two part algorithm described above, provides an unexpectedly effective instrument for performing in vivo histopathological interpretation of colonic mucosa for colorectal cancer screening.

Figures 7A, 7B, 7C:
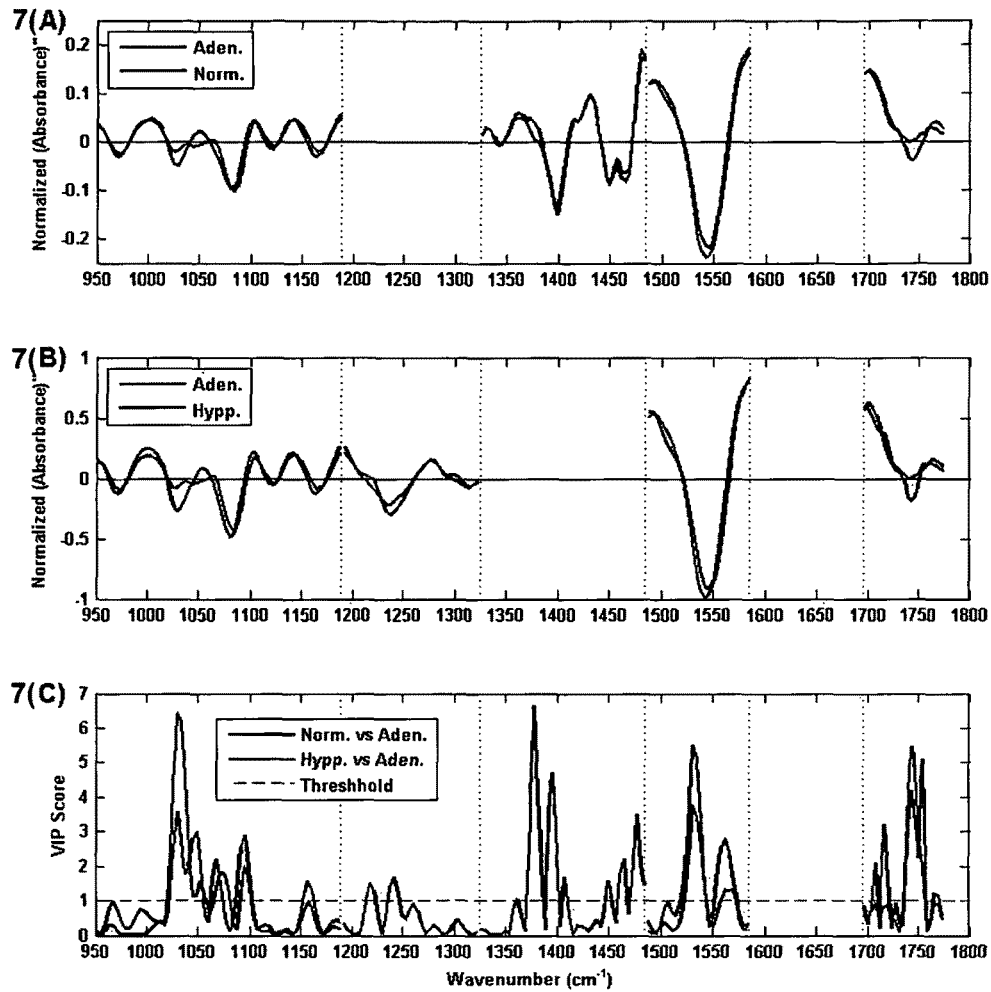
FIGS. 7(A), 7(B) and 7(C)—SHF dataset mean preprocessed spectra by tissue class for (A) NvA model and (B) HvA model. Spectra are divided into subranges and preprocessed without unit-variance scaling as described in text. (C) Variable importance in projection (VIP) scores for NvA and HvA models.

The spectral data input to the PLSDA regression are shown by class average in FIG. 7(A) for the NvA model and in FIG. 7(B) for the HvA model. The wavenumber axes now extend to 1800 $cm^{-1}$ (wavelength approximately 5.6 microns) because subrange 6 (lipids) was used. Again, in neither case did the optimal model include the subrange 5 (Amide I—water). The NvA model applied Savitzky-Golay second derivative preprocessing to subranges 1, 3, 4, and 6 with window lengths of 11, 7, 15, and 11 points, respectively. These subranges were then normalized as a single spectrum using the two-norm. The NvA model utilized three latent variables. Second derivative preprocessing was applied to subranges 1, 2, 4, and 6 in the HvA model, with window lengths of 11, 11, 15, and 11 points. Again, normalization was performed using the entire spectrum, but here using the max-norm. The HvA model utilized four latent variables.

As already demonstrated in the ZSC dataset and previous studies, the glycogen and phosphate peaks of subrange 1 are very important for discriminating adenomas (FIG. 7(C)). The best two-part model utilizing subrange 1 had an accuracy of 73%. The improvement which came with using additional subranges was greater for the SHF dataset (73% to 90%) than the ZSC dataset (78% to 86%). The VIP scores in FIG. 7(C) show that the lipid peak in subrange 6 was quite valuable for discriminating adenomas from both normal mucosa and hyperplastic polyps. While models for both ZSC and SHF utilized subrange 4 (Amide II protein) to about the same extent, the SHF models utilized subranges 2 and 3 much differently. Subrange 2 (amide III protein and phosphates) was used only in the HvA model, while the information in subrange 3 (proteins and lipids) was used only in the NvA model, and was as valuable as any other subrange for discriminating adenoma and normal tissue.

Unit-Variance Scaling

The experiments discussed here used a single spectrometer but different ATR attachments. As can be seen in FIG. 1, there are clear differences in the mean spectra collected with the zinc selenide crystal and the silver halide probe. While it is unlikely that two spectrometers with the same type of ATR attachment would differ as much, the use of a classification algorithm that minimizes the amount of information required for calibration transfer between instruments is desirable. For this reason, the results that did not utilize unit-variance scaling have been emphasized. However, if unit-variance scaling provides clearly better performance, and the difficulty of calibration transfer is no greater (the regression coefficients must be transferred either way), then unit-variance scaling should be employed as a preprocessing component. While the effect of unit-variance scaling on calibration transfer cannot be determined with our current experimental set-up, the effect on performance can assessed.

For the ZSC dataset, no performance improvement was realized with the use of unit-variance scaling. The accuracy was unchanged at 86%, although a smaller number of latent variables (two for both NvA and HvA) were required to achieve this accuracy. Apparently, the scaling process removes some extraneous variance in the spectral data that is extracted by latent variables in the models presented above. The results with unit-variance scaling of the ZSC dataset are not graphically presented here.

Figure 8:
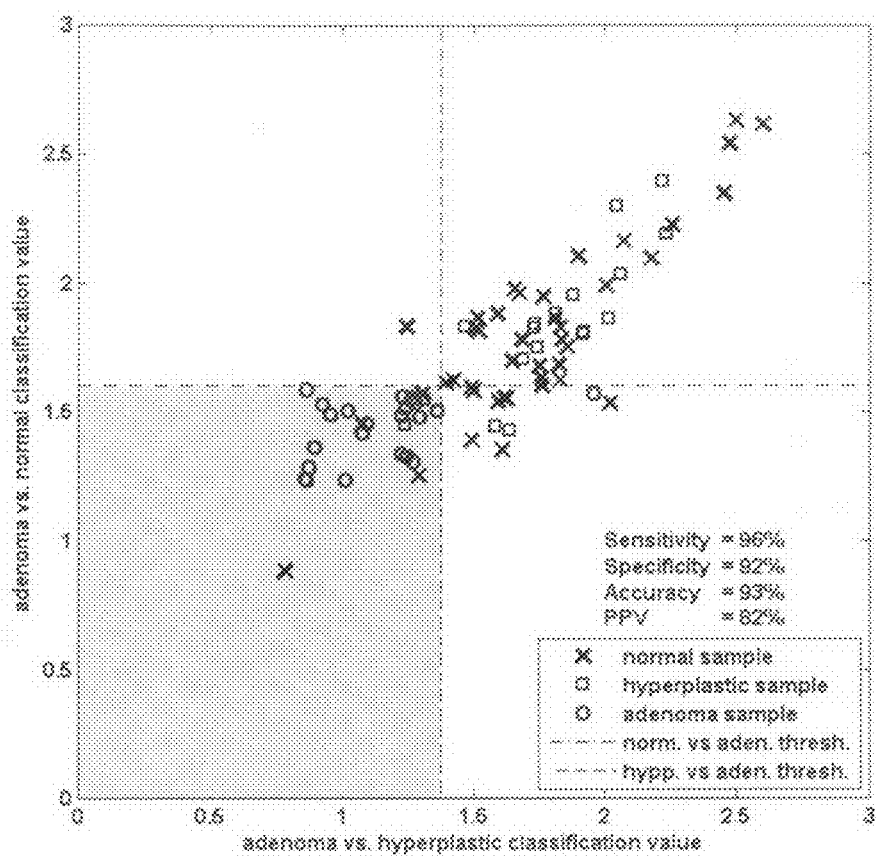
FIG. 8—Best two-part algorithm classification values for silver halide fiber (SHF) dataset. The normal vs. adenoma (NvA) and hyperplastic polyp vs. adenoma (HvA) models both employed unit-variance scaling. The optimal threshold selections for the NvA and HvA models are shown, and correspond to the dot on the ROC curve in FIG. 9. True positives for adenoma appear as circles in the shaded area. True negatives for non-adenoma appear as crosses (normal) and squares (hyperplastic) in the un-shaded area.
Figure 9:
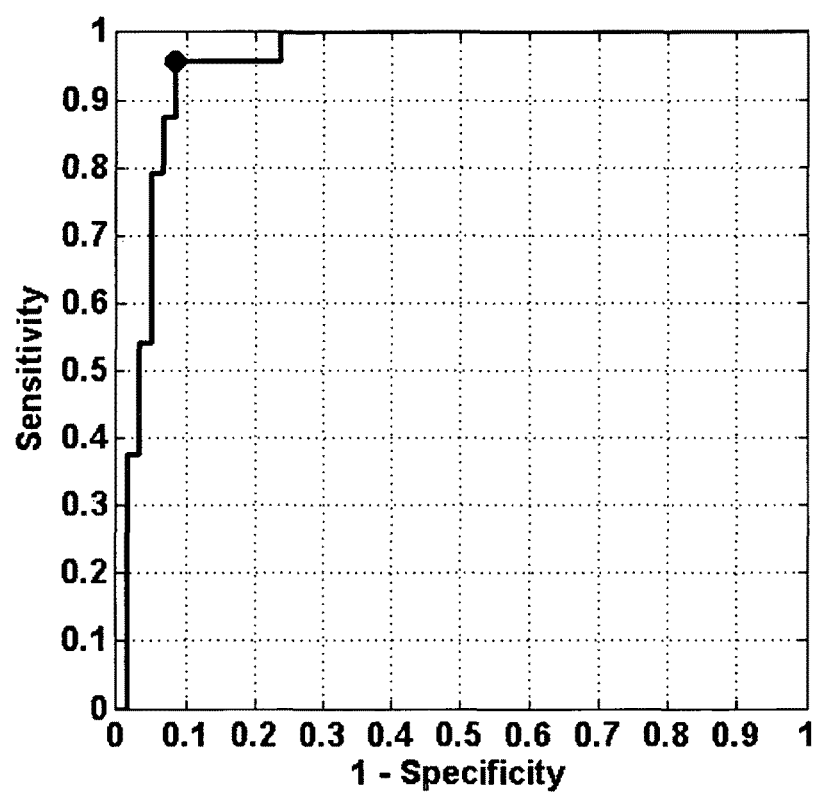
FIG. 9—Receiver operating characteristic of the best two-part algorithm with unit-variance scaling for the SHF dataset. The dot along the curve corresponds to the threshold selections in FIG. 8.

For the SHF dataset, a slight improvement in performance was observed. The classification values are shown in FIG. 8, which is very similar to FIG. 5. The sensitivity was unchanged at 96%. Still, in FIG. 9 the optimal point on the ROC curve has moved toward the upper left corner of the plot. The specificity improved to 92%, the accuracy to 93%, and the PPV to 82%. Performance against hyperplastic polyps was unchanged—the improvement in performance was limited to the normal samples.

Figures 10A, 10B, 10C:
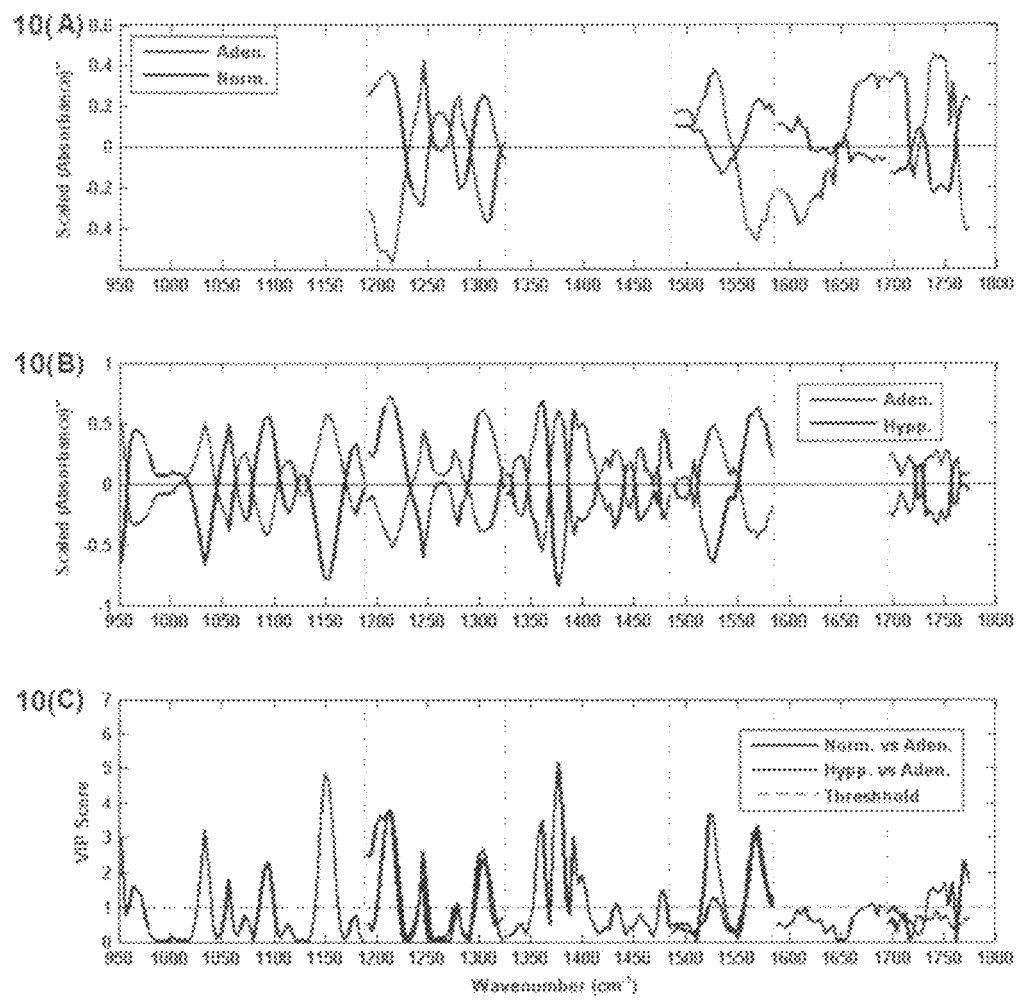
FIGS. 10(A), 10(B) and 10(C)—SHF dataset mean preprocessed spectra by tissue class for (A) NvA model and (B) HvA model. Spectra are divided into subranges and preprocessed without unit-variance scaling as described in text. (C) Variable importance in projection (VIP) scores for NvA and HvA models

The spectral data for input to the PLSDA regression are shown by class average in FIGS. 10(A), 10(B) and 10(C)a for the NvA model and in FIGS. 10(A), 10(B) and 10(C)b for the HvA model. For the first time, the optimal model included the subrange 5 (Amide I—water), but in the NvA model only. This model used subranges 4 and 5 with baseline-removal only, while 15- and 11-point Savitzky-Golay second derivative preprocessing was applied to subranges 2 and 6, respectively. Each subrange was normalized by itself using the one-norm. By normalizing each section independently and then scaling spectral values at each wavenumber by standard deviation, the mixture of units presented a combination of baseline-only and second derivative is eliminated. The HvA model excluded subrange 5 only. Subrange 4 was used with baseline-removal, while Savitzky-Golay second derivative preprocessing was applied to subranges 1, 2, 3, and 6 with window lengths of 11, 15, 7, and 7 points, respectively. The HvA model used the same normalization scheme as the NvA model. The NvA and HvA models both employed only two latent variables, again suggesting that the scaling process removes extraneous variance otherwise captured by additional latent variables.

The VIP scores in FIGS. 10(A), 10(B) and 10(C)c indicate that the glycogen peaks in subrange 1 are still important for predicting class membership. However, the relative importance of the glycogen peaks within this subrange has changed as the unit-variance scaling has placed them on equal footing. In general, the use of unit-variance scaling increases the predictive importance of most subranges relative to subrange 1.

As can been seen in FIG. 8, the HvA model does an excellent job identifying the normal samples as non-adenoma, and excellent performance could be obtained by employing the HvA model without the NvA model. It is notable that subrange 1 is not included in the NvA model at all. Furthermore, subrange 3 is not included in the NvA model, while it is an important component of the HvA model. In the SHF models with scaling presented above, subrange 3 (proteins and lipids) was very important to the NvA model, while it was excluded from the HvA model. Apparently, as a result of the exhaustive search of NvA and HvA model combinations, the selected HvA model does the "heavy lifting" for both non-adenoma tissue classes, while the NvA model is optimized for those small number of normal samples which are not correctly identified by the HvA model.

INDUSTRIAL APPLICABILITY

These results show that adenoma can be discriminated from hyperplastic polyps and normal mucosa with an accuracy of about 85% using an FTIR spectrometer equipped with a zinc selenide crystal ATR device. We expected that performance would decrease when a silver halide fiber optic probe was used for ATR, but in fact, unexpectedly, performance increased to 90% accuracy. The exhaustive search for optimal spectral subranges and preprocessing techniques demonstrated that, in addition to the well-known glycogen, nucleic acid, and Amide protein peaks, there is useful information in the lipids and weaker protein vibrations. The issue of classifier confusion due to the spectral peak of water can be eliminated by completely avoiding the Amide I peak. Much of the information in the various spectral peaks is highly correlated, a problem for which PLSDA is highly suited. There are many different combinations of spectral peaks that provide similar performance. The best algorithm for discriminating adenomatous polyps from both hyperplastic polyps and normal mucosa was found by selecting models for normal and hyperplastic polyp identification that emphasize slightly different features of the spectra.

What is claimed is:

1. A process for determining whether tissue is precancer tissues, benign tissues or normal, comprising:

obtaining a spectrum of a tissue in a first set of subranges of wave numbers, wherein said first set of subranges distinguishes between benign and precancer tissues, and in a second set of subranges of wave numbers, wherein said second set of subranges distinguishes between normal and precancer tissues;

first classifying said tissue as precancer or benign using said first set of subranges;

second classifying said tissue as precancer or normal using said second set of subranges; and determining said tissue is precancer if said tissue is classified as precancer in both said first classifying step and said second classifying step, and said tissue is non-precancer if said first classifying step classifies said tissue as benign regardless of whether said second classifying step classifies said tissue as precancer or normal; and wherein said obtaining step is performed using a device selected from the group consisting of a Fourier transform infrared spectrometer using broad band light, and a spectrometer using a light source selected from the group consisting of multiple narrowband light sources and at least one tunable narrowband light source.

2. A process according to claim 1, wherein said first set of subranges is not the most selective set of subranges for distinguishing between benign tissues and precancer tissues.

3. A process according to claim 1 wherein said second set of subranges is not the most selective set of subranges for distinguishing between normal and precancer tissues.

4. A process according to claim 1, wherein said first set of subranges and said second set of subranges include wavelengths of approximately 5.6 to 5.9, 6.3 to 6.7 and 8.4 to 10.5 microns.

5. A process according to claim 1, wherein said first set of subranges includes wavelengths of approximately 7.6 to approximately 8.4 microns.

6. A process according to claim 1, wherein said second set of subranges includes wavelengths of approximately 6.7 to approximately 7.6 microns.

7. A process according to claim 1, wherein both of said first set of subranges and said second set of subranges are within a diagnostic region having wavelengths between approximately 8.3 and approximately 11.1 microns.

8. A process according to any one of claims 5 to 7, wherein one of said subranges is the entirety of between approximately 8.4 and approximately 10.5 microns.

9. A process according to claim 1, wherein both said first set of subranges and said second set of subranges include wavelengths of approximately 8.4 to approximately 10.5 microns;

wherein said first set of subranges includes approximately 7.6 to approximately 8.4 microns; and wherein said second set of subranges includes approximately 6.7 to approximately 7.6 microns.

10. A process according to any one of claims 4 to 9, further comprising:

preprocessing at least one of said subranges by replacing each spectral value with each of the spectral value's second derivative and applying a window width of approximately 0.3 microns to said first subrange.

11. A process according to any one of claims 4 to 9, further comprising:

preprocessing said second subrange by replacing each spectral value with each of the spectral value's second derivative and applying a window width of approximately 0.5 microns.

12. A process for determining whether tissue is precancer or non-precancer, comprising:

obtaining a spectrum from a tissue at a first subrange of between three and five diagnostic wavelengths selected from the group consisting of:
9.7 microns;
9.1 microns;
5.7 microns;
8.7 microns;
8.2 microns; and
a second subrange of between 5.6 microns to 5.9 microns;
classifying said tissue as precancer or non-precancer using said wavelengths and said second subrange; and
wherein said obtaining step is performed using a device selected from the group consisting of a Fourier transform infrared spectrometer using broad band light, and a spectrometer using a light source selected from the group consisting of multiple narrowband light sources and at least one tunable narrowband light source.

13. A process for determining whether tissue is precancer or non-precancer, comprising:
obtaining a spectrum from said a tissue at a first subrange of wavelengths consisting of:
9.7 microns;
9.1 microns; and
5.7 microns; and
a second subrange of between 5.6 microns to 5.9 microns;
classifying said tissue as precancer or non-precancer using said wavelengths and said second subrange; and
wherein said obtaining step is performed using a device selected from the group consisting of a Fourier transform infrared spectrometer using broad band light, and a spectrometer using a light source selected from the group consisting of multiple narrowband light sources and at least one tunable narrowband light source.

14. A process for determining whether tissue is precancer or non-precancer, comprising:
obtaining a spectrum from a tissue at a first subrange of wavelengths consisting of:
9.7 microns;
9.1 microns;
5.7 microns;
8.7 microns; and
a second subrange of between 5.6 microns to 5.9 microns;
classifying said tissue as precancer or non-precancer using said wavelengths and said second subrange; and
wherein said obtaining step is performed using a device selected from the group consisting of a Fourier transform infrared spectrometer using broad band light, and a spectrometer using a light source selected from the group consisting of multiple narrowband light sources and at least one tunable narrowband light source.

15. A process for determining whether tissue is precancer or non-precancer, comprising:
obtaining a spectrum from a tissue at a first subrange of wavelengths consisting of:
9.7 microns;
9.1 microns;
5.7 microns;
8.7 microns;
8.2 microns; and
a second subrange of between 5.6 microns to 5.9 microns;
classifying said tissue as precancer or non-precancer using said wavelengths and said second subrange; and
wherein said obtaining step is performed using a device selected from the group consisting of a Fourier transform infrared spectrometer using broad band light, and a spectrometer using a light source selected from the group consisting of multiple narrowband light sources and at least one tunable narrowband light source.

* * * * *